United States Patent [19]

Davidson

[11] Patent Number: 4,937,262
[45] Date of Patent: Jun. 26, 1990

[54] PLATINUM DERIVATIVES AND CANCER TREATMENTS

[75] Inventor: Bruce C. Davidson, Johannesburg, South Africa

[73] Assignee: EFAMOL Ltd., Surrey, England

[21] Appl. No.: 88,282

[22] Filed: Aug. 24, 1987

[30] Foreign Application Priority Data

Aug. 29, 1986 [GB] United Kingdom ............... 8620917

[51] Int. Cl.$^5$ .................. A61K 31/13; A61K 31/16
[52] U.S. Cl. ................................ 514/492; 514/182; 260/404.5; 260/414; 260/404; 556/137; 552/504
[58] Field of Search ............... 556/137; 260/397.2, 260/414, 404.5, 404; 514/182, 492

[56] References Cited

U.S. PATENT DOCUMENTS 4,438,033 3/1984 Botteghi et al. .............. 260/397.2 X
4,760,155 7/1988 Heffernan et al. ............... 556/137 X

FOREIGN PATENT DOCUMENTS 59911 9/1982 European Pat. Off. ............ 514/492
167310 1/1986 European Pat. Off. ............ 514/492

Primary Examiner—Patrick P. Garvin
Attorney, Agent, or Firm—Nixon & Vanderhye

[57] ABSTRACT

Derivatives of platinum group metals, particularly platinum itself, wherein the metal is linked to one or more pharmaceutically acceptable steroid, fatty acid or other lipophilic residues aiding transport of the metal across cell membranes in the body, particularly fatty acid amine or fatty acid amide groups

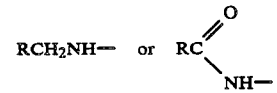

where R is a hydrocarbon group, suitably of 10 to 30 carbon atoms. The derivatives are useful in the treatment of cancer.

10 Claims, No Drawings

PLATINUM DERIVATIVES AND CANCER TREATMENTS

FIELD OF THE INVENTION

The invention relates to heavy metal derivatives and their use in the treatment of various carcinomas.

GENERAL BACKGROUND

Platinum diamine dichloride (variously, cis-platinum, cis-platin, platamine, etc.) has been used as a treatment for certain carcinomas (mainly prostatic) for several years, but suffers from the drawback of requiring large dosages which induce unpleasant side-effects (hair loss, nausea, anaemia, etc.). The compound is believed to work by forming stable complexes with DNA in cell nuclei. This prevents both transcription of the DNA, thus blocking protein synthesis, and replication of the DNA thus inhibiting mitosis. The treatment therefore is not specific for cancer cells only, but also affects cells which normally multiply (bone marrow, skin, gut epithelium, etc.), or synthesise proteins (e.g. liver). The apparent main reason for the high dosages required is the hydrophilic (lipophobic) nature of the compound, and thus the difficulty of its passage through the mainly lipid environment of cell membranes.

Certain unsaturated fatty acids have been shown to have much higher levels of toxicity towards cancer cells than normal cells. The mechanism for this is not clear, but is thought to relate to an impaired capability of cancer cells to metabolise fatty acids normally, and thus an inability to respond properly to exogenous dosage with such fatty acids. The position of the unsaturations in the hydrocarbon chain does not appear to be critical for the production of cytotoxic effects, with the proviso that such unsaturations are desirably methylene-interrupted and that desirably the first unsaturation is in the n-3, n-6, or n-9 position. The number of unsaturations does appear to matter however, with toxicity increasing with number of unsaturations. In general the configuration (cis or trans) of the unsaturations does not have much effect on cytotoxicity. Such fatty acids are obviously highly lipophilic and hydrophobic, thus the generation in vivo of levels high enough to facilitate cytotoxic effects is difficult.

PREFERRED FATTY ACIDS

Preferred unsaturated fatty acids are those of the natural n-6 and n-3 essential fatty acid series as undesired side effects are not to be expected from them. The two series are given below, showing the metabolic pathways.

| n-6 | n-3 |
|---|---|
| 18:2 delta-9,12(linoleic acid) | 18:3 delta-9,12,15 (alpha-linolenic acid) |
| delta-6 desaturase ↓ | |
| 18:3 delta-6,9,12(gamma-linolenic acid) | 18:4 delta-6,9,12,15 |
| elongation ↓ | |
| 20:3 delta-8,11,14(dihomo-gamma-linolenic acid) | 20:4 delta-8,11,14,17 |
| delta-5 desaturase ↓ | |
| 20:4 delta-5,8,11,14(arachidonic acid) | 20:5 delta-5,8,11,14,17 |
| elongation ↓ | |
| 22:4 delta-7,10,13,16(adrenic acid) | 22:5 delta-7,10,13,16,19 |
| delta-5 desaturase ↓ | |
| 22:5 delta-4,7,10,13,16 | 22:6 delta-4,7,10,13,16,19 |

The acids, which naturally are of the all-cis configuration, are systematically named as derivatives of the corresponding octadecanoic, eicosanoic or docosanoic acids e.g. delta $^{9,12}$-octadecadienoic acid or delta $^{4,7,10,13,16,19}$-docosahexaenoic acid, but numerical designation such as, correspondingly, 18:2 n-6 or 22:6 n-3 is convenient. Initials, for example DHA for 22:6 n-3 (docosahexaenoic acid) are also used but do not serve when n-3 and n-6 acids of the same chain length and degree of unsaturation exist (e.g. 22:5 n-6 and 22:5 n-3). Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature, is to the alpha-acid.

The invention provides derivatives of platinum group metals (Ru Rh Pd, Os Ir Pt), particularly platinum itself, wherein the metal is linked to one or more pharmaceutically acceptable steroid, fatty acid or other lipophilic residues aiding transport of the metal across cell membranes in the body, particularly fatty acid amine or fatty acid amide groups

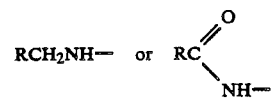

where R is a hydrocarbon group suitably of 10 to 30 carbon atoms.

Preferred subsidiary features of the invention are set out in the claims herein.

In summary, use of the derivatives of the invention makes the platinum or other metal much more lipophilic and thus improves its ability to pass through cell membranes. It is therefore possible to block protein synthesis and cell division with much smaller dosages than with the platinum diamine dichloride alone. Such effects do not require the hydrocarbon chain to be unsaturated. The advantage of using unsaturated fatty acids is that they in themselves also cause cytotoxicity, and thus lower dosages will be cytotoxic by a combination of the DNA blocking effect of the platinum compound and membrane perturbation or other effects of the fatty acids. Moreover, as the fatty acid effect is particular to the cancer cells, the combination may be expected to be lethal to cancer cells alone.

SYNTHESES

Two methods of preparing fatty acid amides

(R=fatty acid "tail") have been used:

(A) 10 g fatty acid+2 ml thionyl chloride+50 ml chloroform+3 drops dimethyl formamide. Reflux for 100 minutes to give acyl chloride. Distil off solvent. Cool to 0° C. Add 20ml NH$_3$. Stand 20 mins.+30 ml CHCl$_3$. Stand 1 hour. Suction filter. Wash with CHCl$_3$. Rotary evaporate. Recrystallise from ethanol.

(B) 10 g fatty acid in 100 ml methanol. Bubble freshly generated HCl for 15 mins. Stand 5 mins. Rotary evaporate. Wash with methanol at 0° C. Redissolve 0.5 g product in 30 ml CHCl$_3$ on ice. Add 7 ml NH$_3$. Stand 30 mins. Rotary evaporate. Recrystallise from ethanol.

Reduction and platinum reaction steps are as follows.

(1) Dissolve 0.5 g fatty acid amide in 30 ml THF and reduce with 0.17 g LiALH$_4$. Reflux at 75° C. for 4 hours. Suction filter. Wash with ether. Rotary evaporate to give the "fatty acid amine" product.

(2) 100 mg PtCl$_4$ in 10 ml H$_2$O+2.4 ml 0.1M HCl. Add 0.2 g amine in 15 ml CHCl$_3$. Mix. Stir overnight. Remove CHCl$_3$ layer. Rotary evaporate. Recrystallise the platinum derivative.

The above has been performed with linoleic acid as substrate, however the same process can be directly applied to the other fatty acids intended as substrates.

PURIFICATION

The material has been purified by thin layer chromatography (TLC) and 3 fractions found. Molecular mass studies indicate these are platinum trichloro linoleoylamine (fraction [1]), platinum dichloro dilinoleoylamine (fraction [2]), and platinum mono chlorotrilinoleoylamine (fraction [3]), approximately 2:1:1 mono- to di- to tri- linoleoylamine. All 3 compounds have been further purified by repeat TLC. (Note: "linoleoyl" in this context is RCH$_2$- derived by reduction of linoleoyl proper

IN VITRO ASSESSMENT

Both the crude mixture and the purified fractions have been assessed in regard to their cytotoxicity. The cell lines used have been derived from a wide range of carcinomas as well as benign, normal and primary cultures.

1. Carcinoma cell lines.

The crude mixture has on molar basis proven to be more effective than either platinum diamine dichloride or the parent fatty acid (linoleic acid). The fractions [2] and [3] produced cytotoxic effects but were not as potent as the crude mixture. Fraction [1] was slightly more potent (+/−10%) than the crude mixture. When a mouse myeloma (SP210) line was used the crude mixture was 3 times as cytotoxic as platinum diamine dichloride, similarly with a malignant fibroblast (3T6D) it was 4 times as potent, with a neuroblastomaglioma hybrid (NG108-15) 5 times, and with a human hepatoma twice as potent.

2. Benign cell lines.

Two benign cell lines (3T3 and 3T6), both fibroblast derived, have been used. Both fraction [1] and the crude mixture proved about twice as potent as platinum diamine dichloride.

3. Normal cell lines.

Normal skin fibroblasts, liver cells, and brain cells maintained in culture exhibited similar susceptibility to fraction [1], crude mixture, or platinum diamine dichloride induced cytotoxicity.

4. Primary culture.

A primary culture of a human ovarian carcinoma was 3 times more susceptible to cytotoxicity induced by the crude mixture and fraction [1] than to platinum diamine dichloride.

DOSAGES

The dosages required in microg/ml culture medium in vitro to produce 50% cell death (LD50) for the 3 fractions, the crude mixture, the parent fatty acid, and platinum diamine dichloride, for all the cell lines used, are shown in Table 1.

TABLE 1

| Cells. | Crude Mix. | [1] | [2] | [3] | Fatty Acid. | PtCl$_2$(NH$_2$)$_2$ |
|---|---|---|---|---|---|---|
| SP210 | 5 | 4 | 16 | 13 | 40 | 16 |
| 3T6D | 3 | 3 | 10 | 10 | 35 | 12 |
| NG108-15 | 3 | 3 | 14 | 17 | 38 | 15 |
| HEP | 8 | 7 | 17 | 15 | 42 | 18 |
| 3T3 | 11 | 10 | 23 | 22 | 53 | 24 |
| 3T6 | 9 | 9 | 21 | 22 | 49 | 21 |
| HSF | 28 | 26 | 27 | 32 | 78 | 28 |
| RL | 36 | 36 | 38 | 40 | 84 | 38 |
| RB | 24 | 22 | 25 | 22 | 62 | 24 |
| HOC | 9 | 10 | 33 | 26 | 28 | 26 |

SP210=mouse myeloma, 3T6D=malignant fibroblast, NG108-15=neuroblastomaglioma hybrid, HEP=human hepatoma, 3T3=benign fibroblast, 3T6=benign fibroblast, HSF=normal human skin fibroblast, RL=normal rat liver, RB=normal rat brain, HOC=primary human ovarian carcinoma.

IN VIVO ASSESSMENTS

Promising preliminary indications have been gained using carcinomas transplanted into nude mice.

I claim:

1. The platinum compound in which platinum is linked to a pharmaceutically acceptable fatty acid residue which aids transport of the metal across cell membranes in the body, said residue being a fatty acid amine or fatty acid amide group of the formula:

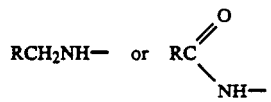

where R is a hydrocarbon group having 10 to 30 carbon atoms.

2. The platinum compound according to claim 1, in which the carbon atoms form a straight chain and the chain contains at least one ethylenic saturation.

3. The platinum compound according to claim 2, in which the chain has at least two methylene interrupted ethylenic unsaturations starting at the n-3, n-6 or n-9 position.

4. The platinum compound according to claim 1, in which R represents the hydrocarbon chain of an unsaturated essential fatty acid of the natural n-6 or n-3 series.

5. A pharmaceutical composition for the treatment of cancer comprising a platinum compound of claim 1 together with a pharmaceutically acceptable carrier or diluent.

6. The pharmaceutical composition of claim 5 in unit dosage form, containing from 100 micrograms to 10 grams of the platinum compound.

7. A method of treating cancer comprising administering to a person having ovarian or hepatic cancer a platinum compound of claim 1 in an amount effective to inhibit cancer cell multiplication.

8. The method of claim 7, in which the amount administered is from about 100 micrograms to 10 grams daily.

9. A method of enhancing transport of platinum group metals across cell membranes in the body wherein said platinum group metal is administered as a compound according to claim 1, in an an amount effective to enhance said transfer.

10. A method according to claim 9, wherein the amount administered is from about 100 micrograms to about 10 grams daily.

* * * * *